(12) United States Patent
Caldwell et al.

(10) Patent No.: US 6,908,430 B2
(45) Date of Patent: Jun. 21, 2005

(54) HAND ACCESS PORT DEVICE

(75) Inventors: Martin Caldwell, Ranelagh Dublin (IE); Christopher Cummins, Tullamore (IE)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 468 days.

(21) Appl. No.: 10/052,297

(22) Filed: Jan. 18, 2002

(65) Prior Publication Data

US 2002/0068923 A1 Jun. 6, 2002

Related U.S. Application Data

(63) Continuation of application No. PCT/IE00/00092, filed on Jul. 28, 2000.

(30) Foreign Application Priority Data

Jul. 30, 1999 (IE) .............................................. S990660
Sep. 24, 1999 (IE) ................................................ 990795

(51) Int. Cl.$^7$ ................................................ A61B 1/32
(52) U.S. Cl. ...................................... 600/207; 606/213
(58) Field of Search .............................. 600/201, 206, 600/207, 208, 235, 231, 233; 606/213, 217

(56) References Cited

U.S. PATENT DOCUMENTS

| | | | | |
|---|---|---|---|---|
| 5,522,791 A | * | 6/1996 | Leyva ........................ | 600/207 |
| 5,636,645 A | | 6/1997 | Ou | |
| 5,803,923 A | | 9/1998 | Bonadio | |
| 5,813,409 A | | 9/1998 | Leahy et al. | |
| 5,899,208 A | * | 5/1999 | Bonadio ..................... | 128/897 |
| 5,906,577 A | | 5/1999 | Beane et al. | |
| 6,033,426 A | * | 3/2000 | Kaji ............................ | 606/213 |
| 6,033,428 A | * | 3/2000 | Sardella ...................... | 606/213 |
| 6,254,534 B1 | * | 7/2001 | Butler et al. ................ | 600/208 |
| 6,623,426 B2 | * | 9/2003 | Bonadio et al. ............ | 600/207 |

FOREIGN PATENT DOCUMENTS

WO     WO 95/07056     3/1995

OTHER PUBLICATIONS

WO 95 22289 A (Bonadio Frank; Gaya Ltd (IE)) Aug. 24, 1995 cited in the application p. 24, line 24–line 33; figure 19.
WO 98 35614 A (Medical Creative Technologies; Dexterity Inc (US); Crook Berwyn M) Aug. 20, 1998 p. 7, line 10–line13; p. 8, line 6–line 10; figure 1.
WO 97 11642 A (Gen Surgical Innovations Inc) Apr. 3, 1997 p. 27, line 1–line 6; figure 28.

* cited by examiner

*Primary Examiner*—Eduardo C. Robert
(74) *Attorney, Agent, or Firm*—Richard L. Myers; Kenneth K. Vu

(57) ABSTRACT

An access port device is provided which enables hand access to a patient's body cavity while retaining pneumoperitoneum by minimizing gas leakage through the access port device. In one embodiment, the access port device includes first and second sleeves forming an inflatable chamber and a third sleeve mounted within the second sleeve including an elastic band for sealingly engaging a hand or wrist. The access port device may also include an exit opening seal for positioning within the patient's body cavity and a second sleeve retraction prevention device for preventing inadvertent movement of the second sleeve outwardly from the patient's body cavity through the incision. In another embodiment, an access port device provided which includes an inner annular sealing device and a non-adhesive outer annular sealing device for creating a non-adhesive seal against the outer surface of a patient. An access component forming an inflatable chamber and including an integral sleeved glove may also be provided. In another embodiment, a sealing force applying feature includes a biasing surface formed on a generally flat annular extension and exposed to gas pressure in an adjacent gas chamber positioned to receive leakage gas leakage between the access port device an the patient to create sealing forces which tend to enhance the seal between the flexible annular extension and patient's skin.

13 Claims, 13 Drawing Sheets

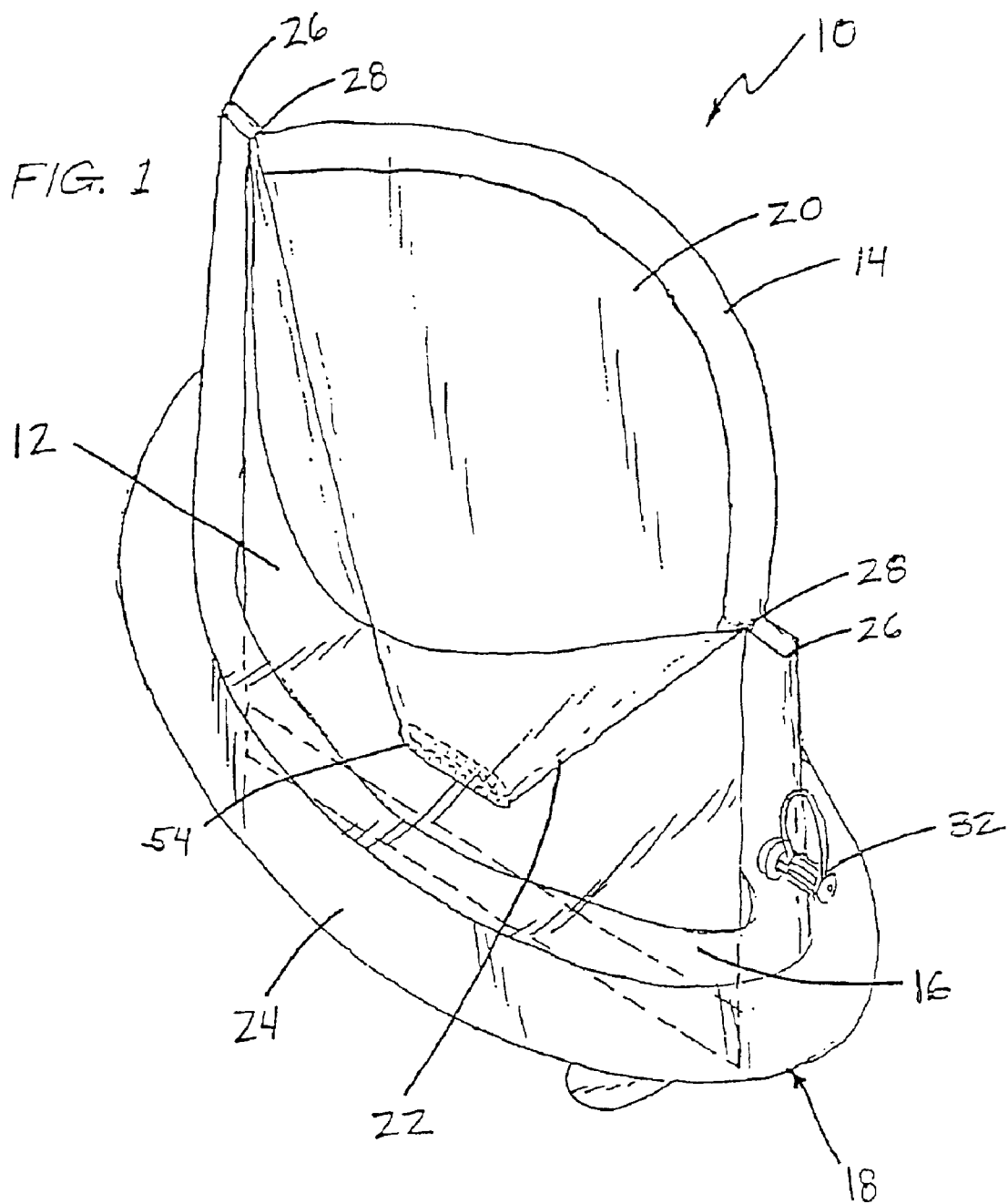

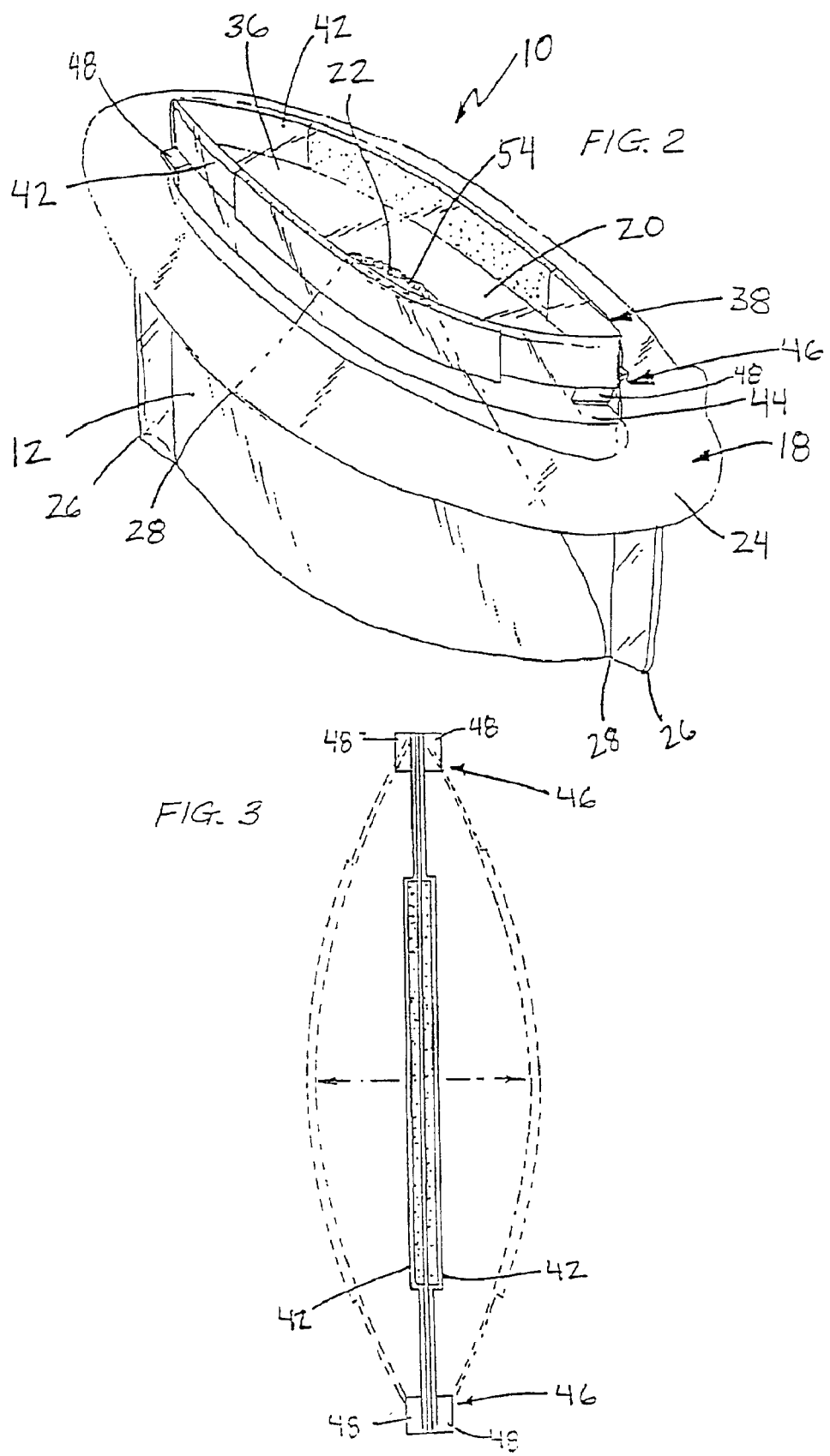

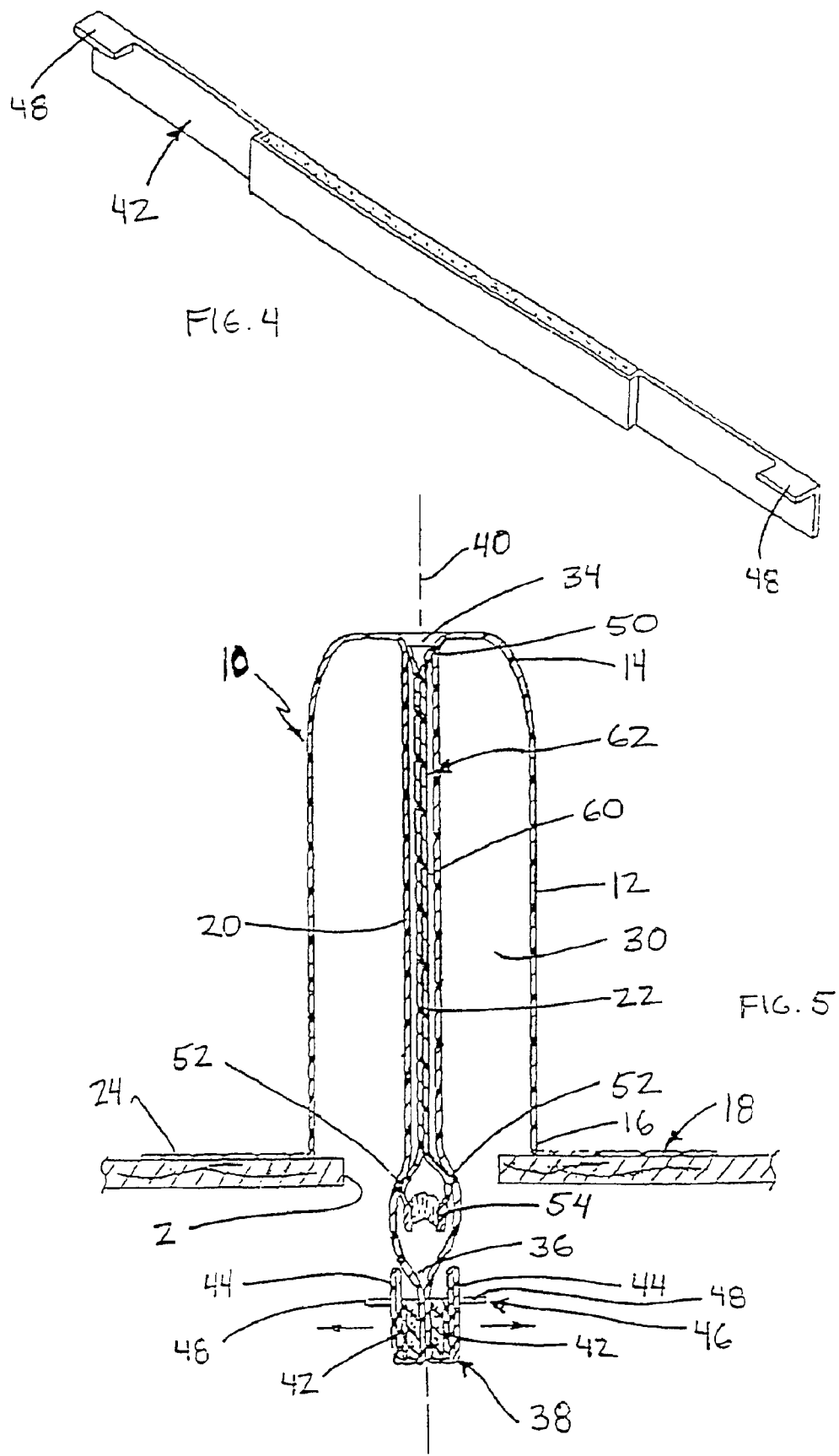

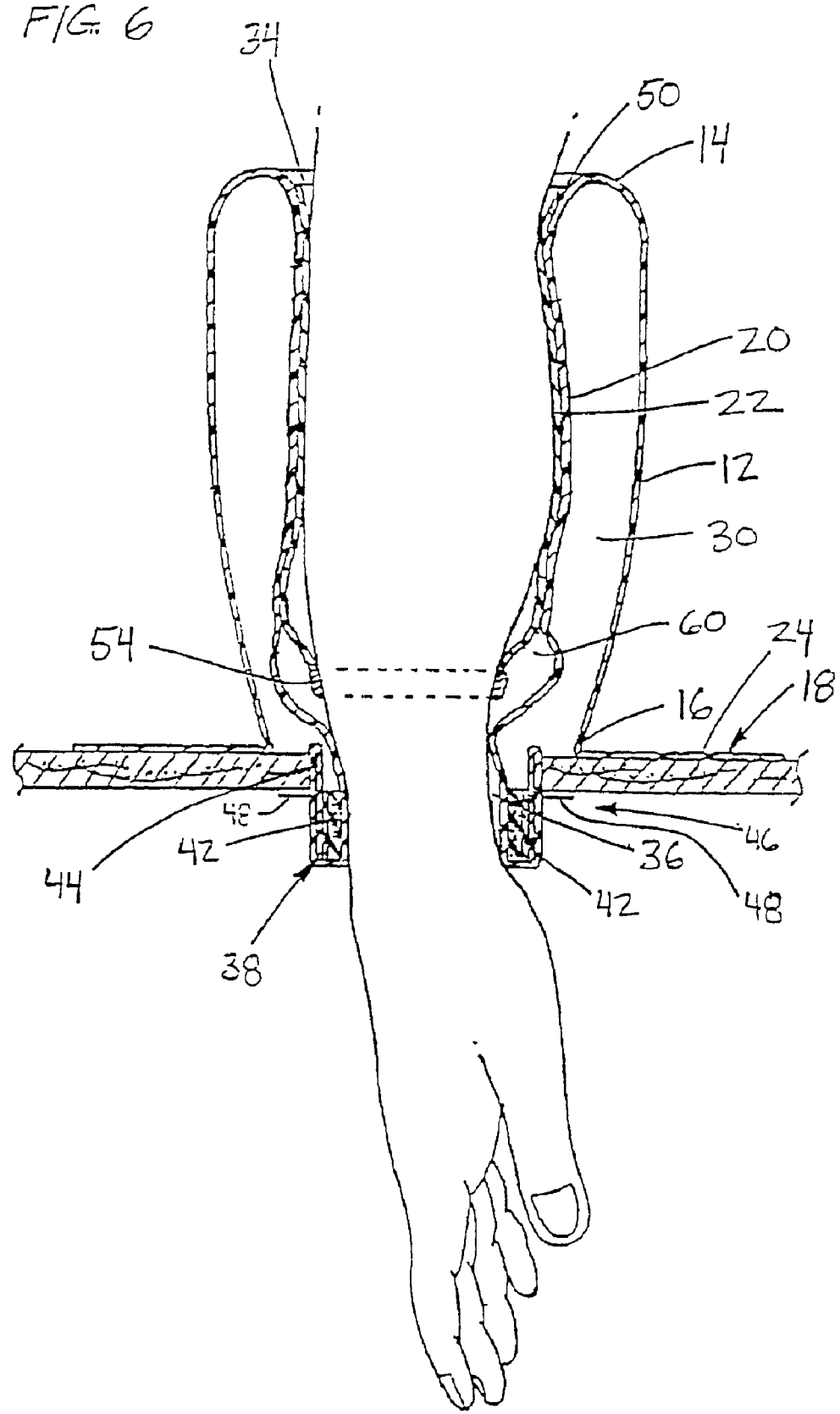

ved Irish Patent Application No.
HAND ACCESS PORT DEVICE

This is a continuation of PCT/IE/00/00092, filed Jul. 28, 2000, which claims priority to Irish Patent Application No. S1999/0660, now granted Irish Patent Application No. S81897, filed Jul. 30, 1999, entitled "A Surgical Device," and Irish Patent Application No. 1999/0795, filed Sep. 24, 1999, entitled "Hand Access Port Device."

FIELD OF THE INVENTION

The present invention relates to an improved hand access port, which enables hand access during laproscopic surgery while retaining pneumoperitoneum.

DISCUSSION OF THE RELEVANT ART

Minimally invasive surgery is carried out by causing a minimum amount of trauma by incision in a patient's body. This type of surgery almost invariably involves deliberately introducing gas into a patient's peritoneal cavity to cause pneumoperitoneum.

Accordingly, surgical sleeves have been developed to prevent gas from escaping from the patient's body cavity while allowing the surgeon to operate using minimally invasive surgery techniques. These sleeves create a controlled pressurized environment within the sleeve while allowing the surgeon's arm to ass through the sleeve. For example, U.S. Pat. Nos. 5,803,921 and 5,899,208 both disclose an access port device having an inner sleeve, an outer sleeve, an exit opening sealing feature for preventing substantial leakage of gas from the patient's body in the region of an exit opening and an entry opening sealing feature substantially preventing gas leakage around the surgeon's arm at the entry opening. A lower annular edge of the outer sleeve is sealingly secured, for example by adhesive, either to wrapping material applied to the patient or directly to the patient's skin. The exit opening sealing feature includes a pair of arcuate bands positioned to bring the opposing faces of the sleeve into contact to form an initial seal. The arcuate bands are passed through the incision into the abdomen. During pressurization, the arcuate bands also function to prevent the tendency of the inner sleeve to invert under pressure since the bands cannot pass back through the incision. The entry opening sealing feature includes an inflatable chamber formed between the sleeves to cause the walls of the inner sleeve to contact and form an entrance seal.

Although the devices disclosed in the '921 and '208 patents operate effectively in many applications, improvements are desirable. For example, in the certain applications, the arcuate bands of the exit opening sealing means tend to shift outwardly from the abdomen through the incision thereby adversely affecting the seal. Also, when a surgeon extends a hand through the entrance seal formed by the inner walls of the sleeve, the inner walls may not effectively contact and seal around the entire outer annular surface of the wrist/arm. As result, an excessive amount of gas is leaked from the patient's body cavity. In addition, improvements in sealing the lower edge of the outer sleeve to prevent leakage would be advantageous.

Another known sleeve is shown in PCT Patent Application No. PCT/IE94/00045 entitled "Apparatus for use in surgery". The access port sleeve shown is used to create a controlled pressurized environment within the sleeve while allowing a surgeon's arm to pass through the sleeve. During surgery, gas is pumped into the body cavity around the surgery site and the sleeve prevents gas escaping while allowing the surgeon to operate using minimally invasive surgery techniques. The application shows a sleeve having a flange at a distal end provided with adhesive for adhering the device to a patient's body or alternatively a mounting ring to surround the incision in a patient's body. While providing a suitable apparatus for performing such surgery the device described suffers from the principle disadvantage that in use, the sleeve protrudes upwardly from the patient and may interfere with the surgical team's activities. Additionally, the sleeve must be sealed against the surgeon's upper forearm by clamping the device to the arm sufficiently tightly to avoid gas leak around the area of the seal. This presents the surgeon with a problem both in sealing the sleeve and in subsequent mobility.

A further problem associated with the use of sleeves of the kind described is that a phenomenon known as "tenting" may occur. "Tenting" means that when the sleeve is adhered to the patient's skin or to a surgical drape and gas is induced into the patients abdominal cavity, there is a tendency for the sleeve to fill with gas and to pull away from the patient. A still further problem associated with the use of such sleeves is that repeated insertion of surgical devices or the surgeons hand can cause unacceptably high trauma levels around the incision. This is particularly problematic when a surgeon attempts to remove an intact specimen or a hard organ.

Therefore, there is a need for an improved access port device for more effectively preventing gas from escaping from the patient's body while allowing the surgeon to effectively operate using minimally invasive surgery techniques.

Therefore, it is an object of the present invention to overcome the disadvantages of the prior art and to provide an access port device capable of permitting effective surgery while permitting body cavity pressure to be easily maintained.

It is another object of the present invention to provide an access port device capable of minimizing leakage of gas from the body cavity between the access port device and a surgeon's hand/arm in a simple manner without limiting the movement of the hand.

It is yet another object of the present invention is to provide an access port device, which effectively prevents inadvertent retraction of a sleeve of the device from a body cavity.

Yet another object of the present invention is to provide an access port device capable of creating a gas tight seal between the access port device and patient's body.

Still another object of the present invention is to provide an access port device capable of effectively minimizing gas leakage from a body cavity through the space between the access port device and the patient's body.

A further object of the present invention is to provide an access port device, which creates an effective seal without the use of adhesive.

SUMMARY OF THE INVENTION

These and other objects of the present invention are achieved by providing an access port device for use in surgery, comprising a first sleeve of flexible material including a proximal end and a distal end, a securing device attached to the distal end of the first sleeve to secure the access port device externally to the patient and a second sleeve of flexible material attached to the proximal end of the first sleeve. The second sleeve includes an entry opening adjacent the proximal end of the first sleeve and an exit opening positioned a spaced distance from the entry opening. An inflatable chamber is formed between the first and second sleeves. The access port device further includes a third sleeve of flexible material attached to at least one of the first and second sleeves wherein the third sleeve includes an annular elastic band positioned between the entry and the exit openings of the second sleeve to sealingly engage a surgeon's arm extending through the third sleeve. The third sleeve is preferably formed of a sufficient length to be positioned adjacent the exit opening and extends along a substantial portion of the second sleeve. Also, the third sleeve may be attached to the second sleeve at a first attachment location adjacent the entry opening, and at a second attachment location a spaced distance along the second sleeve from the first attachment location. The elastic band is preferably positioned at a distal end of the third sleeve.

The access port may include an elongated exit opening seal mounted on the second sleeve at the exit opening. The exit opening seal is positioned along an exit opening seal plane extending through the entry opening, and the exit opening of the second sleeve. A second sleeve retraction prevention device may be included for preventing inadvertent retraction of the second sleeve from an incision in a patient's body. The second sleeve retraction prevention device includes at least one transverse wing extending transverse to the exit opening seal plane. The at least one transverse wing includes at least one first wing positioned on a first side of the exit opening and at least one second wing positioned on a second side of the exit opening. Each of the at least one first wings and the at least one second wings may include a pair of wings. The wings may be integrally formed on the elongated exit opening seal. The elongated exit opening seal may include a pair of opposed bands biased together while the transverse wing may be integrally formed on at least one band of the opposed bands. The first pair of wings may be located at a first end of the pair of opposed bands while the second pair of wings is located at a second end of the pair of opposed bands. One wing of each pair of wings extends from the bands in a first transverse direction while the other wing extends from the other band in a second transverse direction opposite to the first direction.

In another embodiment, the access port device of the present invention comprises a sleeve of flexible material including a proximal end and a distal end, and forming an access opening positionable in an incision in a patient's body. The device further includes an outer annular seating device attached to the proximal end of the sleeve to secure the access port device externally to a patient and an inner annular sealing device attached to the distal end of the sleeve to secure the access port device internally to the patient. Moreover, the access port device includes an access component removably connected to the outer annular sealing device and including a flexible ring removably engaging the outer annular sealing device. The access component may include an access sleeve of flexible material, which may include an integral glove for receiving a surgeon's hand. The access sleeve and glove have a length sufficient to extend from the flexible ring through the access opening. The outer annular scaling device may include an annular groove for receiving the flexible ring and the groove may be formed in an outer peripheral surface of the outer annular sealing device. An inflatable chamber may be formed between the sleeve and the access sleeve. The outer annular sealing device may include a flexible annular extension extending radially inwardly from the outer annular scaling device wherein the annular extension includes an inner annular biasing surface facing outwardly from the patient's body. The annular extension may include a circumferentially unsupported annular floating edge. The device may further include a gas chamber positioned adjacent the inner annular biasing surface to collect gas leaking between the sleeve and the patient's body. Preferably, the flexible annular extension is generally flat. The outer annular sealing device may include an upper annular overhang positioned opposite and spaced from the flexible annular extension so that the gas chamber is positioned between the upper annular overhang and the flexible annular extension. The outer annular sealing, device may further include an outer biasing surface facing the inflatable chamber.

Thus, the present invention provides an access port device comprising a first sleeve or flexible material including a proximal end and a distal end and forming an access opening positionable in an incision in a patient's body. The access port device also includes a leakage-minimizing feature for minimizing gas leakage from between the first sleeve and the patient's body. The leakage minimizing feature includes an outer annular sealing device attached to the proximal end of the first sleeve, an inner annular sealing device attached to the distal end of the first sleeve for abutting and sealingly engaging an inner surface of a body cavity of the patient, and a seal force applying device for causing leakage gas between the first sleeve and the patient's body to apply a sealing force against the outer annular sealing device to bias the outer annular sealing device toward the patient. The access port device may further include a second sleeve of flexible material positioned adjacent the first sleeve and an inflatable chamber formed between the first and second sleeves. The sealing force applying device may further include the flexible annular extension and the inner biasing surface. The sealing force applying device may further include sizing the first sleeve to fit closely to the patient's cavity wall to cause a sealing force to bias the outer annular sealing device into scaling engagement with the patient's skin. The sealing force applying device may further include the annular overhang, gas chamber and outer biasing surfaces mentioned hereinabove.

The present invention also provides an access port device for use in surgery which comprises a sleeve of flexible material, a non adhesive outer annular sealing device attached to a proximal end of the sleeve and adapted to create a non adhesive, substantially gas tight seal adjacent the patient's body to prevent gas flow from the patient's body and an inner annular sealing device attached to the distal end of the sleeve to secure the access port device internally to the patient. In this case, the access component is sealingly mounted on the outer annular sealing device and extendable into the access opening. The access component may be removably mounted on the outer annular sealing device, which may, in turn, include the flexible annular extension.

According to one aspect of the invention there is provided a surgical device for use in minimally invasive surgery of the type using an inflated body cavity accessible to a surgeon through an incision, the device being formed to define a sleeve access port for insertion into the incision and having:
  mounting means for locating and securing the device in position on a patient;
  sealing means to prevent substantial leakage of gas from the body cavity; and
  a retractor to limit contact between the sleeve and the incision when in use.

Thus, contact with the incision is limited thereby reducing patient trauma and greatly improving the ease with which instruments or a surgeon's hand may be inserted.

In one arrangement, the retractor is provided as a deformable tube.

Preferably, the tube has at opposing ends a proximal ring and a distal ring.

Preferably, the proximal and distal rings are formed for substantially airtight engagement with the sleeve and with the patient's abdomen.

In one arrangement the or each ring incorporates an adhesive portion for fixing the ring in position.

Preferably, the distal ring is formed for substantially airtight engagement with the sleeve and with the patient's internal abdominal wall.

Ideally engagement between the proximal ring and sleeve is provided by a skirt carried on the sleeve and having a rim formed for releasable engagement to the ring.

In one arrangement the ring and skirt are integrally formed.

In one arrangement the skirt has an integrally formed glove or pocket for receiving a surgeons hand or surgical instrument.

In one arrangement the skirt has a recessed or undercut receiver formed for engagement with a ring or a surgeons glove.

In a preferred embodiment, the proximal ring incorporates a flexible gas retaining ring extending down from the proximal ring and formed for engagement against a patients skin when in position to define a gas retention chamber.

Preferably, the gas retaining ring is inflatably movable between an insertion position and an in use position.

In one arrangement, the gas retaining ring is provided by a collapsible bellows ring.

In a particularly preferred embodiment, the device incorporates a retractor-positioning device.

Ideally, the retractor-positioning device has means for releaseably engaging the proximal ring and the distal ring.

Preferably, the means for engaging the proximal ring and the distal ring are movable between a retracted position and a locating position.

Ideally, the means for engaging the proximal ring and the distal ring are telescopically movable.

According to another aspect of the invention the proximal ring supports a flexible web said web in turn defining a hole for receiving the sleeve.

According to a further aspect of the invention the device incorporates a collapsible support scaffold, the scaffold being formed for supporting the device in an operative state and collapsible to provide a surgeon free access to the incision.

DESCRIPTION OF THE DRAWING

The invention will now be described more particularly with reference to the accompanying drawings, which show, by way of example only, some embodiments of a surgical device in accordance with the invention, in which:

FIG. 1 is a perspective view of a first embodiment of the access port device of the present invention;

FIG. 2 is a perspective view of the bottom of the first embodiment of FIG. 1;

FIG. 3 is a plan view of the opposed bands of the exit opening seal;

FIG. 4 is a perspective view of one of the bands of the exit opening seal;

FIG. 5 is a cross sectional side view of the access port of the first embodiment as applied to a patient prior to access during, surgery;

FIG. 6 is a cross sectional side view similar to FIG. 5 during use with access by a surgeon's arm;

DESCRIPTION OF THE INVENTION

Figure 7:
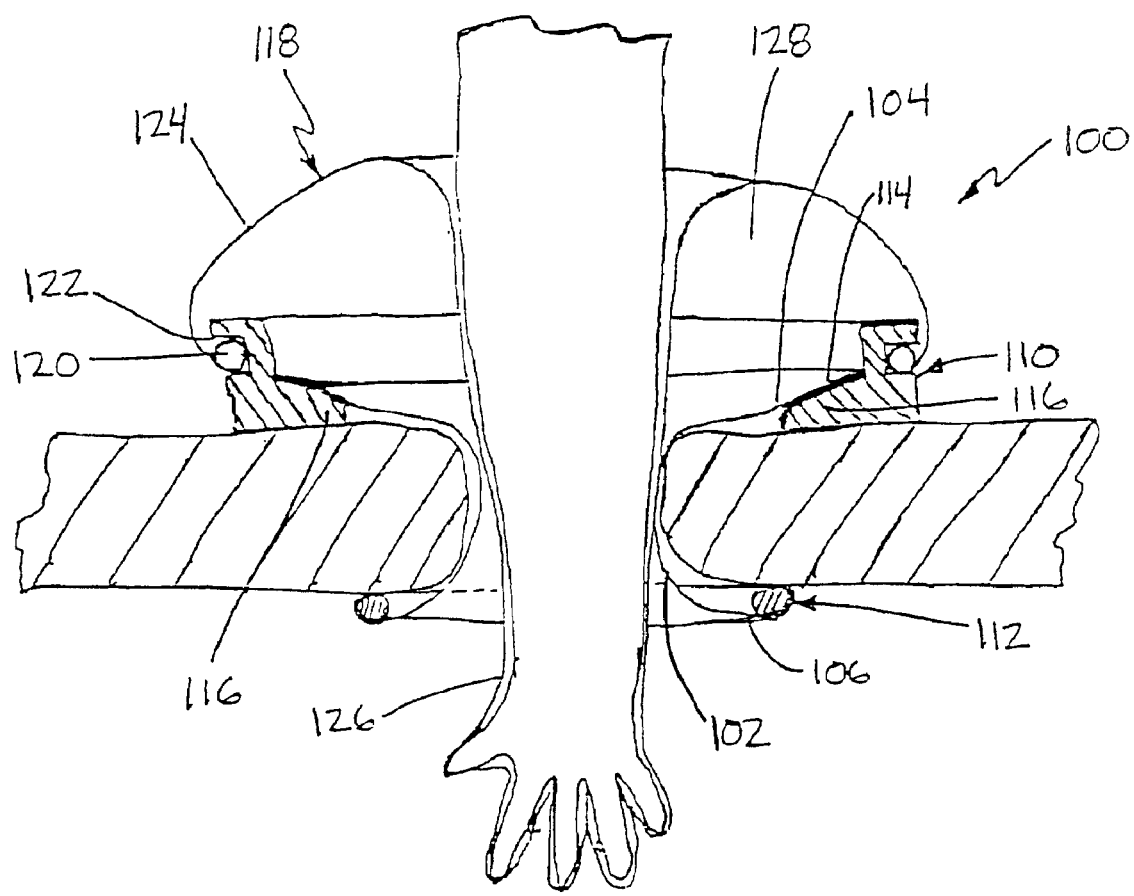
FIG. 7 is a cross sectional view of a second embodiment of the present invention in use.

Referring to FIGS. 1–6, there is shown a first embodiment of the access port device of the present invention, indicated generally at 10, for permitting access to a patient's body cavity during surgery while maintaining body cavity pressure. Access port device 10 generally includes a first sleeve 12 of flexible material including a proximal end 14 and a distal end 16, a securing device 18 attached to the distal end 16 of first sleeve 12, a second sleeve 20 attached to proximal end 14 of first sleeve 12 and a third sleeve 22 of flexible material attached to at least one of the first sleeve 12 and second sleeve 20. As described hereinbelow, this arrangement can be effectively and sealingly attached to a patient's body surrounding an incision to permit the insertion of a hand into a patient's body cavity while simply and effectively maintaining pneumoperitoneum as desired throughout a laproscopic surgery procedure.

Referring to FIGS. 1 and 5, both first sleeve 12 and second sleeve 20, extend annularly with second sleeve 20 positioned inside first sleeve 12. Second sleeve 20 is preferably integrally formed at proximal end 14 of first sleeve 12, i.e. second sleeve 20 is an integral extension of first sleeve 12 turned inwardly onto itself. Securing device 18 includes a flange 24 extending transversely from distal end 16 for connection to either the patient's skin or wrapping material covering the patient's skin. Preferably, the flange 24 includes an adhesive, such as a solid or a liquid adhesive, for adhering to the wrapping material or skin to securely and sealingly affix the access port device 10 to the patient. Both first sleeve 12 and second sleeve 20 may each be formed from opposing sheets of flexible material fused together along opposite edges 26 and 28, respectively, with edges 26 being positioned outwardly from edges 28. As shown in FIG. 5, an inflatable chamber 30 (FIG. 5) is positioned between first sleeve 12 and second sleeve 20 for receiving pressurized gas via an inlet valve 32 (FIG. 1). Inlet valve 32 is provided on first sleeve 12 so that inflatable chamber 30 can be inflated prior to the insertion of a surgeon's hand into the device as shown in FIG. 5. The gas pressure in inflatable chamber 30 is maintained by gas flowing from the body cavity of the patient during pneumoperitoneum. Thus, after the inflation of chamber 30 through valve 32, valve 32 is closed.

Referring to FIG. 5, the second sleeve 20 forms an entry opening 34 positioned adjacent the proximal end 14 of first sleeve 12 and an exit opening 36 positioned a spaced distance from entry opening 34. Second sleeve 20 has a length sufficient to extend through first sleeve 12 and through an incision 2 formed in a patient's body 4 so as to be positioned in the patient's body cavity when access port device 10 is applied to the patient as shown in FIG. 5. Access port device 10 further includes an elongated exit opening seal 38 mounted on second sleeve 20 and extending across exit opening 36. Elongated exit opening seal 38 is positioned along an exit opening seal plane, indicated at 40, which extends through entry opening 34 and exit opening 36 of second sleeve 20. Elongated exit opening seal 38 includes a pair of resilient opposed bands 42 as clearly shown in FIGS. 2, 3 and 5. Each band 42 is positioned in a respective elongated cuff 44 formed in the distal end of second sleeve 20. Bands 42 are formed of a resilient flexible material, i.e. plastic, which permits the bands to be flexed outwardly to create an exit opening for receiving a surgeon's hand and/or an instrument. Each of the bands 42 may also include a cushioning strip made from, for example, foam, to provide more comfort to the surgeon's hand/wrist during use. In the relaxed state, the bands 42 are biased together bringing the opposing faces of second sleeve 20 into mutual contact and hence forming an exit opening seal. The geometry of bands 42 is such that, when presented at right angles to the incision 2, it is possible for the bands to pass through the incision. Once in position within the patient's body cavity, bands 42 align themselves nominally parallel to the abdominal wall as shown in FIG. 5. Thus, elongated exit opening seal 38 functions to form an initial seal preventing the escape of gas from the body cavity to the atmosphere via the exit opening, 36 of second sleeve 20.

Access port device 10 also includes a second sleeve retraction prevention feature, indicated generally at 46, for preventing inadvertent retraction of second sleeve 20 from incision 2. It has been found that during use of conventional access port devices, the insulflation pressure in the patient's body cavity acts to undesirably invert the inner sleeve and move the inner sleeve outwardly through the incision. Second sleeve retraction prevention feature 46 of the present invention effectively prevents elongated exit opening seal 38, and thus the distal end of second sleeve 20, from passing outwardly through incision 2 under the force of the insulflation pressure. As shown in FIGS. 2–5, second sleeve retraction feature 46 includes at least one transverse wing 48 extending from the distal end of second sleeve 20 transverse to exit opening seal plane 40 (FIG. 5). Specifically, in the preferred embodiment, second sleeve retraction prevention feature 46 includes a transverse wing 48 formed at each end of each of the opposed bands 42 as clearly shown in FIG. 3.

Transverse wings 48 are integrally formed on opposed bands 42 and extend transversely generally parallel to the under surface of the patient's body defining the body cavity. The transverse wings 48 extend through respective slits formed in the cuff 44 of second sleeve 20 thereby securing bands 42 within cuff 44. During use, once the distal end of second sleeve 20 has been inserted through incision 2 into the patient's body cavity, transverse wings 48 will prevent inadvertent movement of elongated exit opening seal 38 through incision 2 by abutting the under surface of the patient's body forming the body cavity as shown in FIG. 6. Even prior to insertion of a surgeon's arm into the access port device 10, when insulflation pressure causes movement of exit opening seal 38 toward incision 2, transverse wings 48 will abut the incision and prevent exit opening seal 38 from passing through incision 2. As a result, second sleeve retraction prevention feature 46 creates a more reliable and effectively usable access port device, which can be easily and simply utilized without subsequent repositioning of second sleeve 20 after initial setup.

Importantly, access port device 10 of the present invention also includes the third sleeve 22 positioned within, and attached to, second sleeve 20. In the preferred embodiment, third sleeve 22 extends from entry opening 34 of second sleeve 20 to a location adjacent exit opening 36. Third sleeve 22 is attached to, or integrally formed on, second sleeve 20 at a first attachment 50 adjacent entry opening 34. First attachment 50 extends annularly to prevent gas from escaping from the space between second sleeve 20 and third sleeve 22. Third sleeve 22 is also attached to second sleeve 20 at a second attachment 52 located a spaced distance from first attachment 50 along third sleeve 22. Second attachment 52 occurs at a point close to a distal end of third sleeve 22 so as to maintain the distal end in the inner space of second sleeve 20. For example, second attachment 52 may be in the form of two separate weld lines positioned on opposite sides of third sleeve 22. An inflatable gas chamber 60 is formed between second sleeve 20 and third sleeve 22, which captures gas leaking by elongated exit opening seal 38. The inflation of chambers 30 and 60 create an entry opening seal 62 by forcing the opposing surfaces of third sleeve 22 into abutment prior to use as shown in FIG. 5. Thus the combination of exit opening seal 38 and entry opening seal 62 effectively minimizes gas leakage through access port device 10 so as to retain pneumoperitoneum.

Importantly, third sleeve 22 includes an annular elastic band 54 for sealingly engaging a surgeon's hand, wrist or arm positioned in third sleeve 22 as shown in FIG. 6. In the preferred embodiment, annular elastic band 54 is positioned at the distal end of third sleeve 22. Annular elastic band 54 is sized and designed with sufficient elasticity so as to permit insertion of hands and arms of varying sizes while ensuring a substantially gas tight seal between elastic band 54 and the arm. It will be understood that the size and elasticity of the access port and elastic band 54 can be varied to accommodate, for instance only one finger rather than the entire hand and arm of the surgeon. Also, the size and elasticity of the access port and elastic band 54 may be designed to accommodate instruments of various sizes while still substantially preventing leakage from the patient's body cavity through the access port device 10. It should be noted that the various sleeves of access port device 10 may be manufactured from any flexible, gas impermeable, sterilizable, biocompatible material, for instance polyethylene.

Reference is now made to FIG. 7 which discloses a second embodiment of the present invention directed to an access port device 100 including a first sleeve of flexible material 102 having a proximal end 104 for positioning external to a patient and a distal end 106 for positioning in a patient's body cavity. Access port device 100 includes an outer annular sealing device 110 attached to proximal end 104 of first sleeve 102 and an inner annular sealing device 112 attached to distal end 106 of first sleeve 102. Both outer and inner annular sealing devices 110 and 112 are sized and shaped to extend in an annular fashion around a given incision and, therefore, may be provided in a variety of sizes depending on the length of the incision. Outer annular sealing device 110 includes a biasing surface 114 facing, outwardly away from the patient's body 4. Proximal end 104 of first sleeve 102 is sealingly attached to biasing surface 114 around the entire circumference of outer annular sealing device 110. Likewise, the distal end 106 of first sleeve 102 is sealingly attached to inner annular sealing device 112 in any conventional manner creating a secure sealed connection. Inner annular sealing device 112 may be a ring formed of any flexible resilient material. Biasing surface 114 is preferably formed on a flexible annular extension 116 of outer annular sealing device 110.

Access port device 100 also includes an access component 118 sealingly engaging outer annular sealing device 110 and extendable into the access opening formed by first sleeve 102. Preferably, access component 118 includes a flexible ring 120 designed for removable mounting in an annular groove 122 formed in outer annular sealing device 110. Flexible ring 120 is preferably formed of an elastic, resilient material to permit the ring to be stretched and moved into groove 122 and, if desired, expanded for removal from groove 122. Of course, flexible ring 120 is designed with a circumference and sized relative to the size of outer annular sealing device 110 such that stretching of the ring is required for engaging annular groove 122 so that the ring is biased into sealing engagement with outer annular sealing device 110 in annular groove 122. In the present embodiment, access component 118 also includes a sleeve of flexible material 124 extending from flexible ring 120 and having a length sufficient to extend through the access opening formed by first sleeve 102 and inner annular sealing device 112 as shown in FIG. 7. In the embodiment shown, the sleeve of flexible material 124 may include an integrated glove to form a sleeved glove 126 for receiving a surgeon's hand/arm. As shown in FIG. 7, an inflatable chamber 128 is formed between first sleeve 102 and the sleeve of flexible material 124 for containing gas flowing through the gap between sleeved glove 126 and first sleeve 102 thereby retaining pneumoperitoneum.

The first sleeve 102 is sized to permit inner annular sealing device 112 to be effectively positioned underneath the patient's cavity wall 4 and outer annular sealing device 110 to be positioned on the outer surface of the patient while first sleeve 102 fits closely to the patient's cavity wall. As a result, inner annular sealing device 110 is biased tightly against the inner surface of the patient's body cavity wall 4 while first sleeve 102 exerts a downward force on outer annular sealing device 110. In addition, since biasing surface 114 faces outwardly away from the patient's body cavity wall 4, gas pressure in the inflatable chamber creates gas pressure sealing forces acting on biasing surface 114 which tends to bias outer annular sealing device 110 against the patient. Consequently, an effective seals is achieved between outer annular sealing device 110 and the patient's body Therefore, by sizing first sleeve 102 appropriately and utilizing biasing surface 114, the present access port device 100 creates an effective seal for minimzing gas leakage from the patient's body cavity through the space between access port device 100 and the patient's body cavity wall 4.

Figure 8:
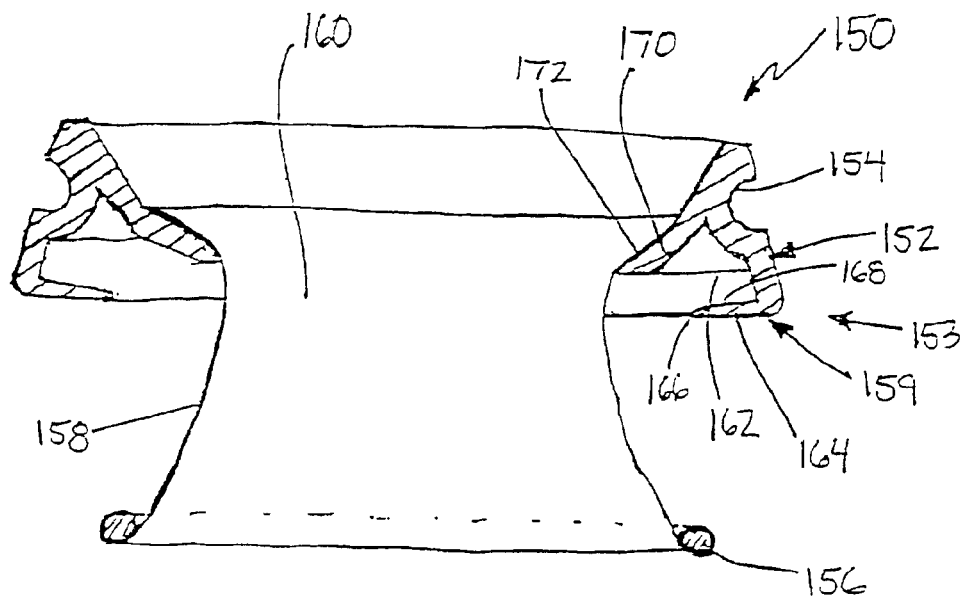
FIG. 8 is a cross sectional view of a third embodiment of the present invention including a seal force applying feature.
Figure 9:
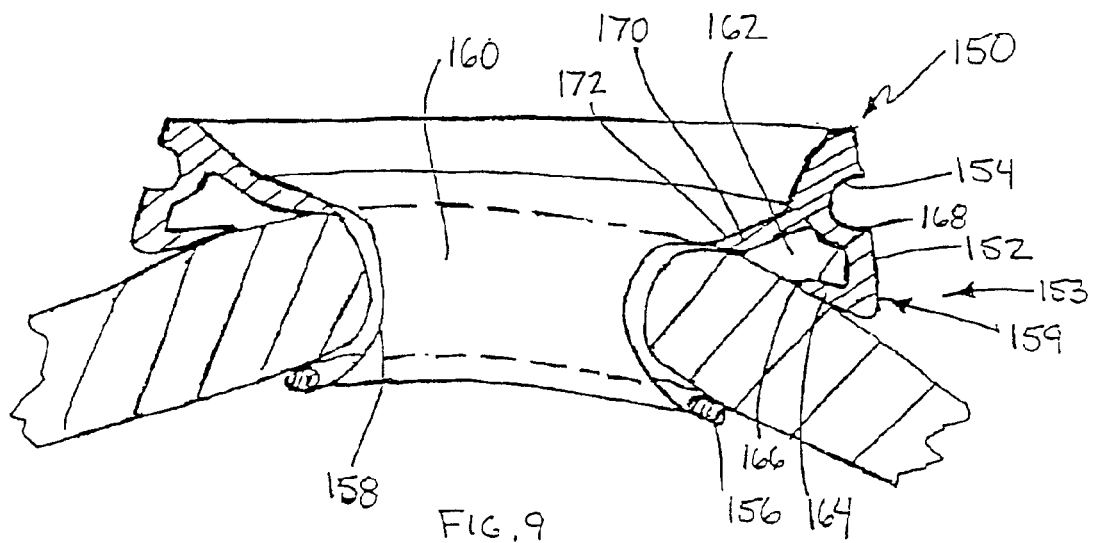
FIG. 9 is a cross sectional view of the device of FIG. 8 during use but without showing an access component attached.
Figure 10:
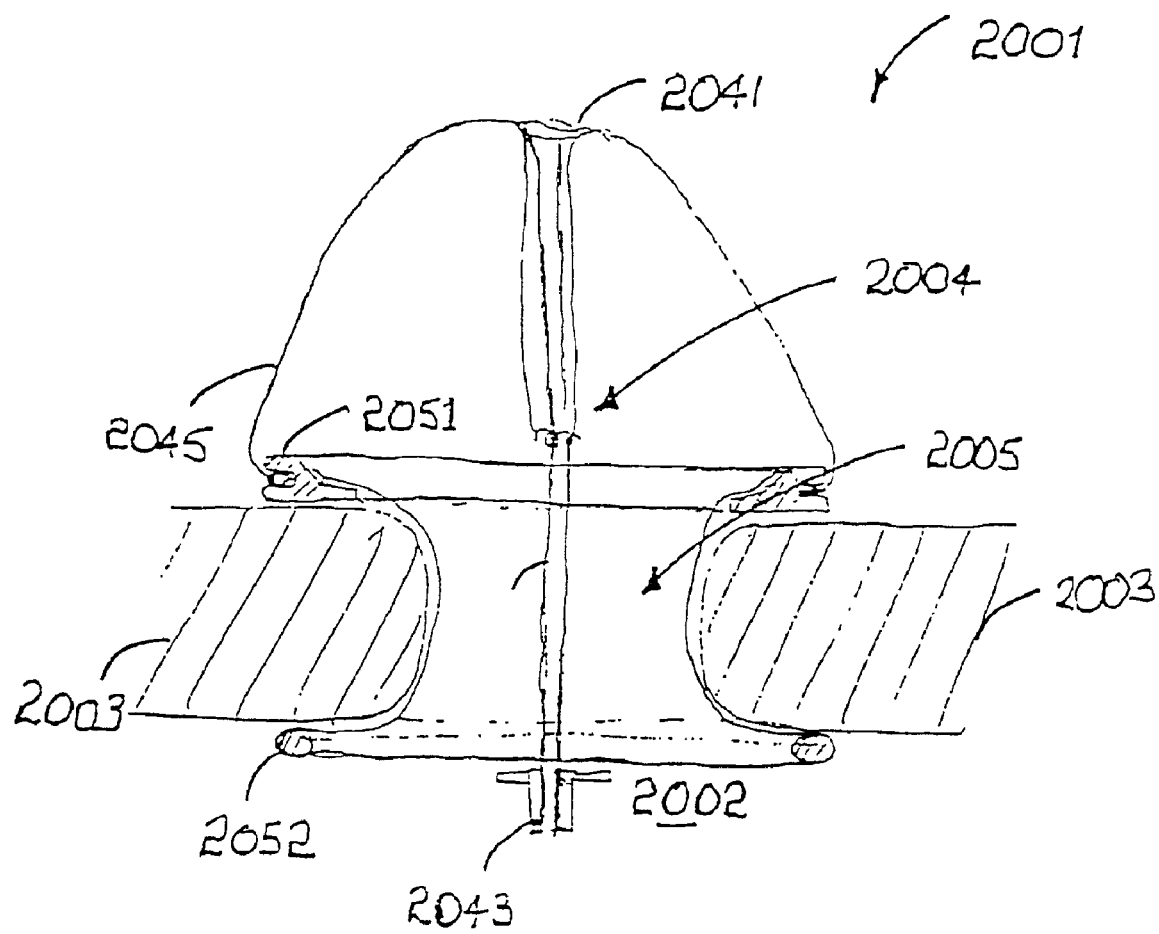
FIG. 10 is a sectional view of a surgical device in accordance with the invention in position on a patient.

FIGS. 8 and 9 disclose a preferred embodiment of an access port device indicated generally at 150, which is similar to the access port device disclosed in the embodiment of FIG. 7 except for a modified outer annular sealing device 152, which creates a ore effective seal against a patient's body in many applications. Similar to the embodiment of FIG. 7, access port device 150 may include an access component ( not shown), such as the sleeved glove 126 of the previous embodiment, which can be sealingly mounted in annular groove 154 of outer annular sealing device 152. Also, access port device 150 include an inner annular sealing device or ring 156 and flexible sleeve 158 forming an access opening, 160 similar to the embodiment of FIG. 7. However, in the present embodiment, access port device 150 includes a leakage minimizing device 153 for minimizing gas leakage from between sleeve 158 and the patient's body, which includes a sealing force applying feature 159 including outer annular sealing device 152 and a leakage gas chamber 162 for receiving leakage gas leaking between access port device 150 and the patient. In addition, outer annular sealing device 152 includes a flexible annular extension 164 having a generally flat shape and extending radially inwardly to form a circumferentially unsupported annular floating edge 166. Flexible annular extension 164 also includes an inner biasing surface 168 facing outwardly from the patient and exposed to gas chamber 162. The outer annular sealing device 152 further includes an overhang 170, which in part forms gas chamber 162 and includes an outer biasing surface 172. The sleeve 158 is sealingly attached to outer biasing surface 172. Therefore, gas chamber 162 is formed between flexible annular extension 164 and overhang 170. It should be noted that overhang 170 may be designed with a sufficient length so as to about the patient's skin when placed on the patient as shown in FIG. 9.

When applied to a patient's body as shown in FIG. 9, the sealing force applying feature 159 effectively minimizes leakage between access port device 150 and the patient's body in the following manner. When the device is attached to the patient, inner annular sealing device 156 lies tight against the inner surface of the patient's body cavity, i.e. abdomen. The flexible sleeve 158 is sized, as dicussed hereinabove with respect to the embodiment of FIG. 7, so as to exert a downward force on outer annular sealing device 152 causing compression of flexible annular extension 164 against the patient's skin or an intermediate material. The access component of FIG. 7 may then be attached to annular groove 154 by stretching flexible ring 120 around outer annular sealing device 152 so as to position ring 120 in groove 154. If the access component is in the form of sleeved glove 126, the surgeon would placed the glove on his hand by inserting his arm into the sleeved glove prior to mounting the access component on outer annular sealing device 152. After placing the glove on his hand, flexible ring 120 would then be placed in annular groove 154 while the surgeon's arm is extended through access opening 160. Also, before attaching the sleeve glove 126 to outer annular sealing device 152, the overall length of the sleeve glove 126 may be adjusted by rolling or unrolling the flexible ring 120 to thereby take-up or release the flexible material from ring 120.

During use, with the patient's body cavity deliberately pressurized by introducing gas as shown in FIG. 9, any leakage gas from the patient's body cavity, leaking between inner annular sealing device 156 and the patient, will flow in the space between sleeve 158 and the patient toward gas chamber 162. This leakage gas will be trapped in gas chamber 162. Gas pressure induced biasing forces are then generated on inner biasing surface 168 so as to bias flexible annular extension 164 into sealing abutment against the patient's skin thereby creating an enhanced seal between flexible annular extension 164 and the patient. The greater the gas pressure in gas chamber 162, the greater the sealing force between flexible annular extension 164 and the patient's skin. As a result, increased leakage into gas chamber 162 not only maintains but tends to enhance the seal between outer annular sealing device 152 and the patient's skin. In the event flexible annular extension 164 lifts away from the patient's skin, inner annular sealing device 156 will remain in contact with the patient's skin thereby maintaining a seal. Also, the gas pressure in the inflatable chamber formed between sleeve 158 and the access component imparts gas pressure induced forces on outer biasing surface 172 tending to bias overhang 170 into abutment with the patient's skin thereby further assisting in sealing against leakage. When it is desired to remove the sleeved glove 126, the surgeon's hand may simply be puller outwardly and removed from sleeved glove 126 or the flexible ring 120 may be first released from outer annular sealing devices 110, 152. Preferably, the seal created between outer annular sealing device 110 due to the effect of leakage minimizing device 153 is sufficient to avoid the use of adhesive between device 153 and the patient, thereby creating a non adhesive sealed access port. If an adhesive is used, which is more likely in the embodiment of FIG. 7, a liquid adhesive may be applied.

Referring to FIGS. 10 to 13 there is illustrated a surgical device according to the invention indicated generally by the reference numeral 2001. The surgical device 2001 is formed for use in minimally invasive surgery of the type using an inflated body cavity indicated generally by the reference numeral 2002. The cavity 2002 is accessible to a surgeon through an access port, defined by a sleeve 2004, which passes through an incision in a patient's abdominal wall 2003. The sleeve 2004 is connected to a retractor indicated generally by the reference numeral 2005 which a traumatically retracts the incision. The retractor 2005 is pressed against the incision to protect it from contact as a surgeon introduces or withdraws a hand, surgical device or body tissue. The retractor 2005 is inserted using a retractor-positioning device indicated generally as 2006, which will be described in more detail below.

Figure 11:
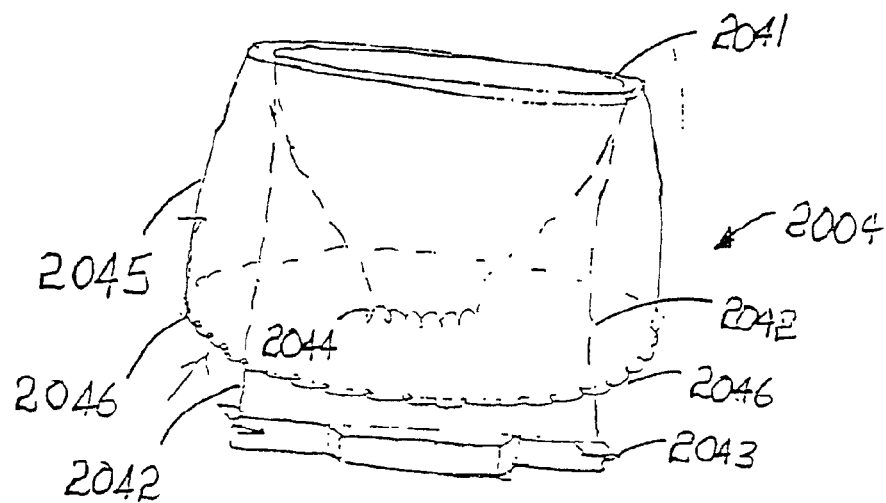
FIG. 11 is front view of a sleeve forming part of the invention.

Referring now to FIG. 11, sealing means is provided for the device 2001 by the sleeve 2004, which is in this case of the type known and marketed by Medtech Ltd., as an INTROMIT R sleeve. The sleeve 2004 has an entrance opening 2041. A flexible elongate inner sleeve 2042 extends downwardly from the opening 2041 and terminates away from the opening with a taut valve 2043. A feathered valve 2044 is also suspended from the opening inside the inner sleeve 2042. The sleeve 2004 also has a skirt 2045 extending downwardly from the opening 2041 outside the inner sleeve 2042. The skirt 2045 has a flexible rim 2046 for connection in an airtight manner to the retractor 2005.

Figure 12:
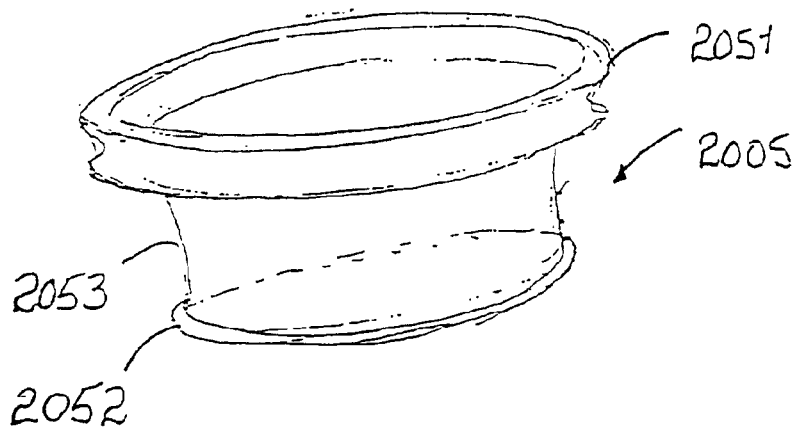
FIG. 12 is a perspective view of a retractor forming part of the invention.
Figure 13:
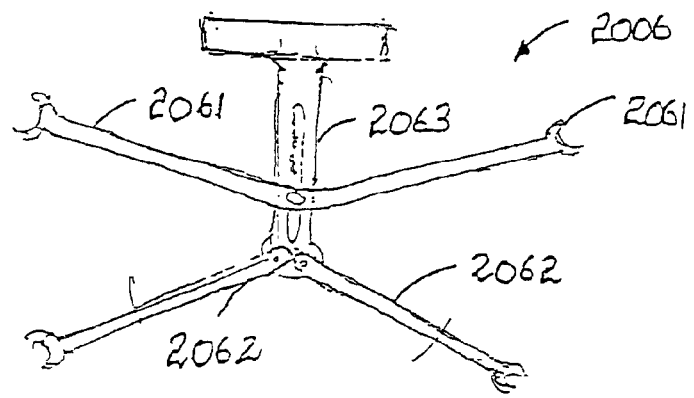
FIG. 13 is a front view of a retractor-positioning device forming pan of the invention.

The retractor 2005 as shown in FIG. 12 has a proximal ring 2051 for receiving the flexible rim 2046 and a distal ring 2052 connected to the proximal ring 2051 with a flexible incision engaging retractor wall 2053. The proximal ring 2051 and the distal ring 2052 are positioned on the patient using the retractor-positioning device 6 as shown in FIG. 13. The retractor-positioning device 2006 has means for engaging the proximal ring 2051 provided by a pair of oppositely directed telescopic arms 2061 carried on an introduction shaft 2063. The shaft 2063 also carries means for engaging the distal ring provided in this case by pivotally moveable distal arms 2063.

In use, an incision is made in the abdominal wall 2003. The distal ring 2052 and the proximal ring 2051 are engaged on the respective arms 2062, 2061 with the arms 2062, 2061 in a retracted position (not shown) having the arms 2062, 2061 close to the shaft 2063. The proximal ring 2051 is then positioned on the patient by telescopically extending the arms 2061. The distal arms 2062 and portion of the shaft 2063 are then passed through the incision into the cavity 2000. The distal ring 2052 is moved into position when in the cavity 2002 by pivoting the oppositely directed arms 2062 away from the shaft 2063 so that the ring 2052 surrounds the incision. The ring 2051 is disengaged from the arms 2061 causing it to open against the abdomen wall. The arms 2062 are disengaged from the ring 2052 by pulling upward. By positioning the retractor in this way a variety of incision depths can be accommodated.

When the retractor 2005 has been positioned on the patient the flexible rim 2046 is then deformed by the surgeon to engage on and around the proximal ring 2051 in an airtight manner. The body cavity is then inflated and when inflated the flexible elongate inner sleeve 2042 is allowed to extend downwardly from the opening 2041 with the taut valve 2043 inserted into the body cavity. The feathered valve 2044 is also suspended from the opening 2041 inside the inner sleeve 2042 and above the incision. The gas pressure within the cavity inflates the skirt 2015. The seal of the rim 2046 and the ring 2051 prevents air pressure from escaping. The surgeon can then operate on the patient and the constant and controlled distance between the sleeve and the retractor prevents unnecessary contact with the incision thereby reducing overall patient trauma and providing the surgeon with a greater range of movement unencumbered by the incision wall.

Figure 14:
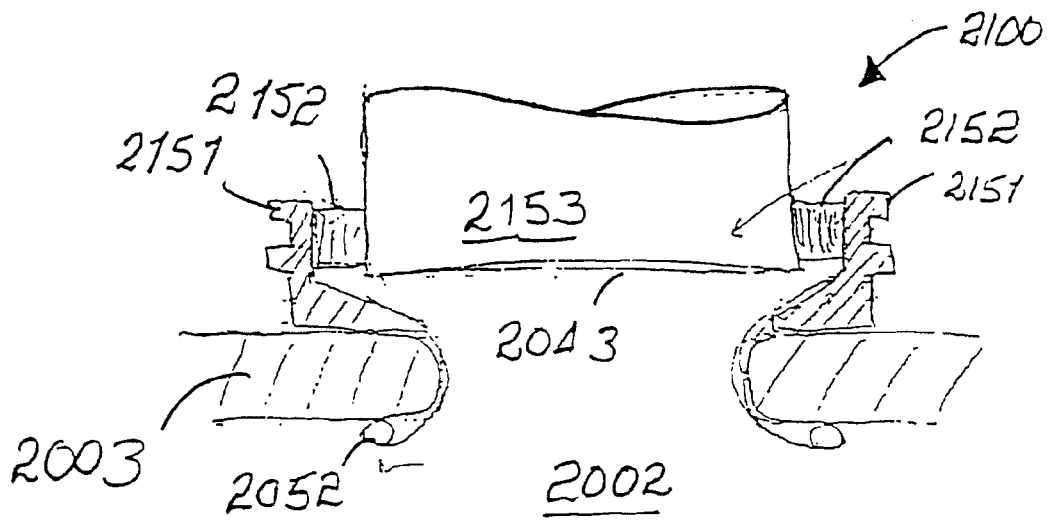
FIG. 14 is a sectional view of another embodiment of a surgical device in accordance with the invention in position on a patient.
Figure 15:
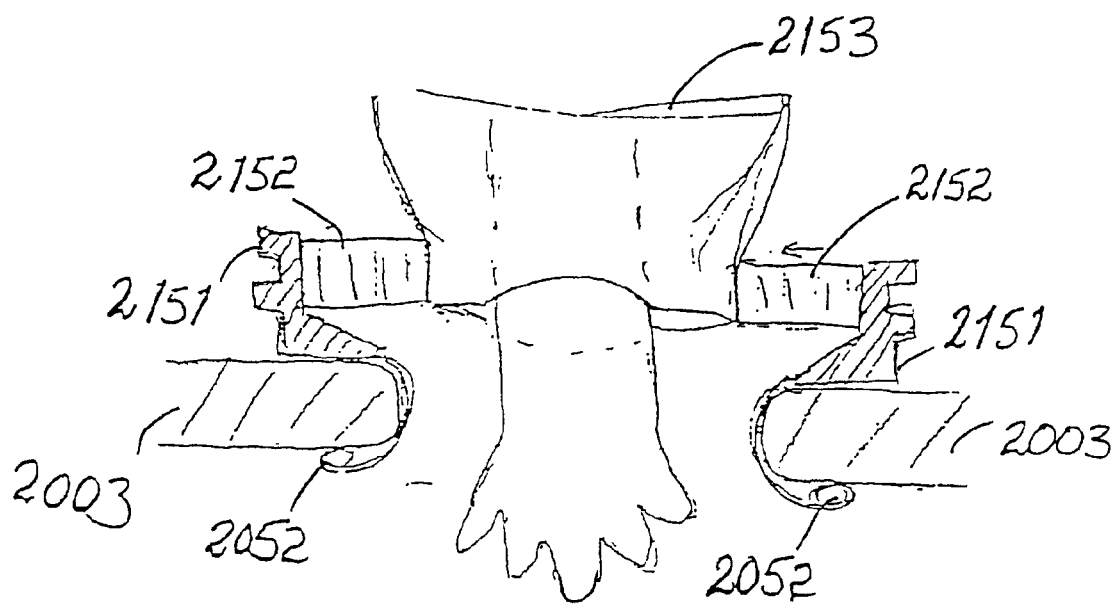
FIG. 15 is a sectional view of the device of FIG. 14 with a surgeon's hand inserted.

Referring now to FIGS. 14 and 15 there is illustrated another surgical device according to the invention, indicated generally by the reference numeral 2100 in which parts similar to those described in FIGS. 10 to 13 are identified by the same reference numerals generally. In this embodiment, the device has an extended proximal ring 2151. The proximal ring 2151 supports a highly flexible web 2152 which in turn defines an opening through which a sleeve 2153 passes. The sleeve 2153 is terminated in a taut valve 2043 above the incision. The operation of this device is similar to that described above. It will be appreciated that the retractor may also be manually positioned on the operating site. By providing the device in this way the taut valve is housed above the incision thereby allowing a surgeon greater visibility as well as eliminating the need to insert any valves within the body cavity. Additionally, the valve will not travel with the surgeon's wrist during insertion and as a low sealing force is required, the surgeon suffers little compression on the arm during insertion.

Figure 16:
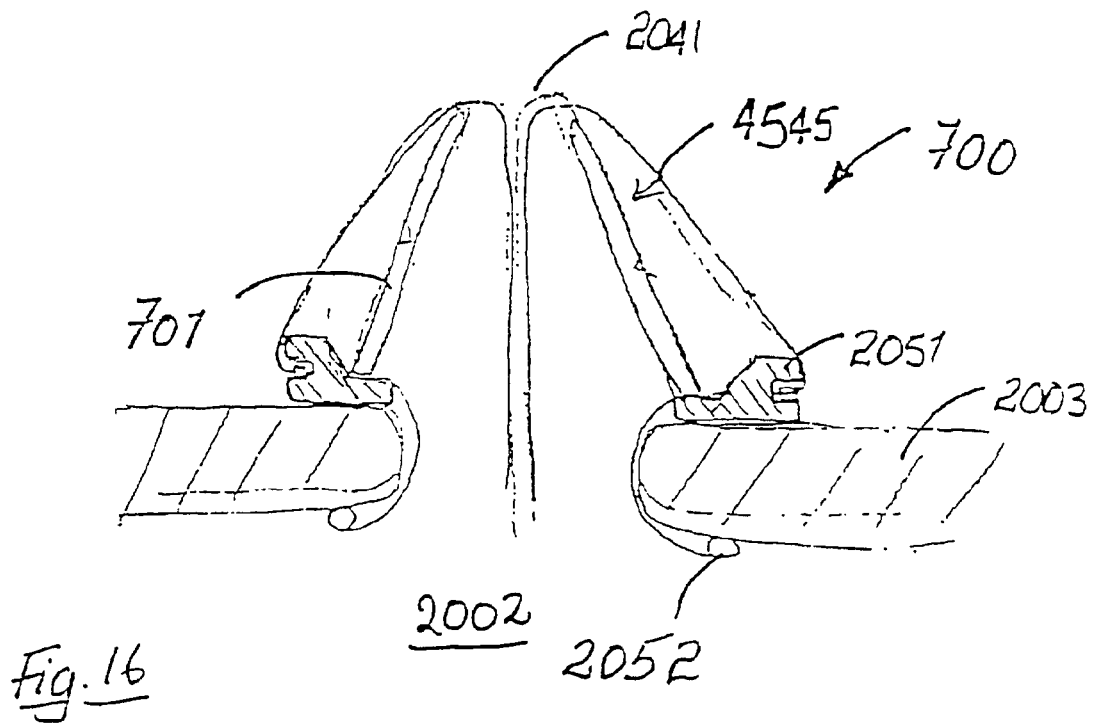
FIG. 16 is a sectional view of a further embodiment of a surgical device in accordance with the invention in position on a patient.
Figure 17:
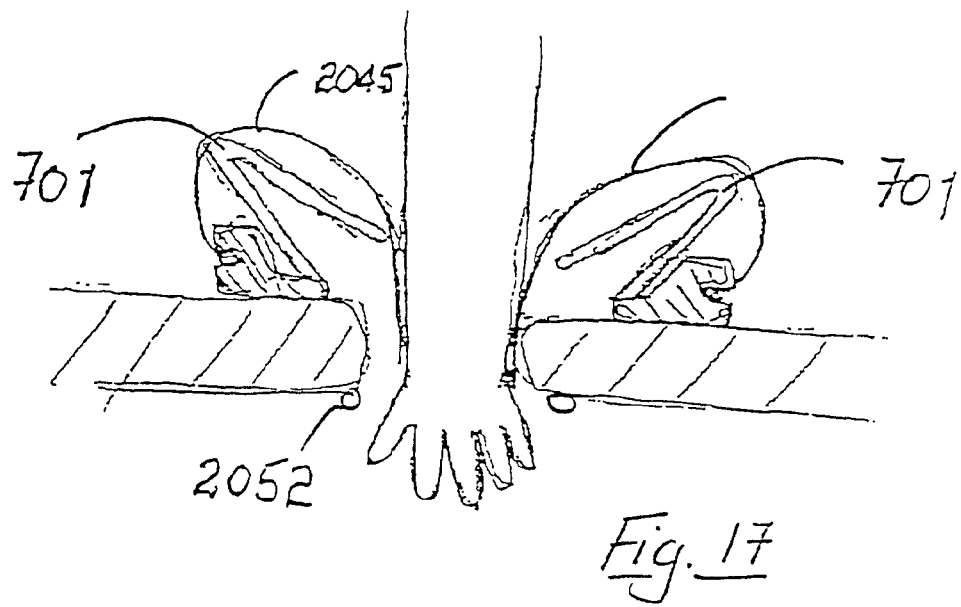
FIG. 17 is a sectional view of the device of FIG. 16 with a surgeons hand inserted.

Referring now to FIGS. 16 and 17 there is illustrated a further surgical device according to the invention, indicated generally by the reference numeral 700 in which parts similar to those described in FIGS. 10 to 15 are identified by the same reference numerals generally. In this embodiment the skirt 2045 is supported by a collapsible scaffold structure 701. The scaffold structure 701 is in turn carried on the proximal ring 2051.

In use, when the device 701 has been positioned on a patient the skirt 2045 is supported by the structure 701 (See FIG. 16). As a surgeon inserts a hand or instrument into the sleeve 2004 the structure collapses (See FIG. 17) to provide free access and good operating site visibility for the surgeon.

Figure 18:
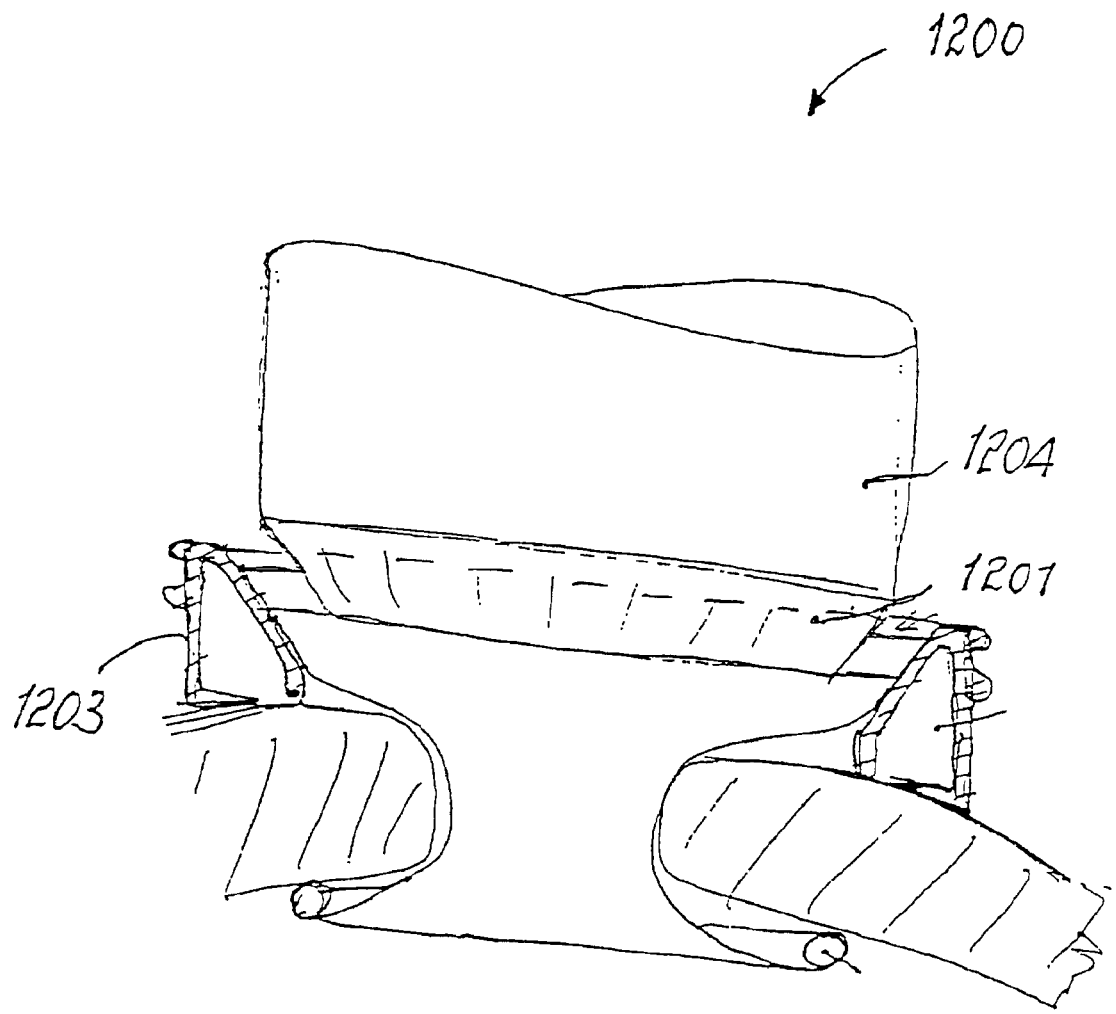
FIG. 18 is a sectional view of another surgical device in accordance with the invention in position on a patient.

FIG. 18 illustrates another a surgical device according to the invention, indicated generally by the reference numeral 1200. In this embodiment a taut valve 1201 is formed from an elasticised portion of a tapered sleeve 1204. Oppositely directed connecting limbs 1202 extend outwardly from the valve 1201 and attach to a proximal ring 1203. In use, the limbs 1202 stretch the sleeve 1204 causing the sleeve 1204 to narrow the taut valve 1201 and seal. When a surgeon inserts a hand or surgical instrument the limbs 1202 are deflected to allow access. When the hand or instrument is removed, the limbs re-establish the seal as before.

Figure 19:
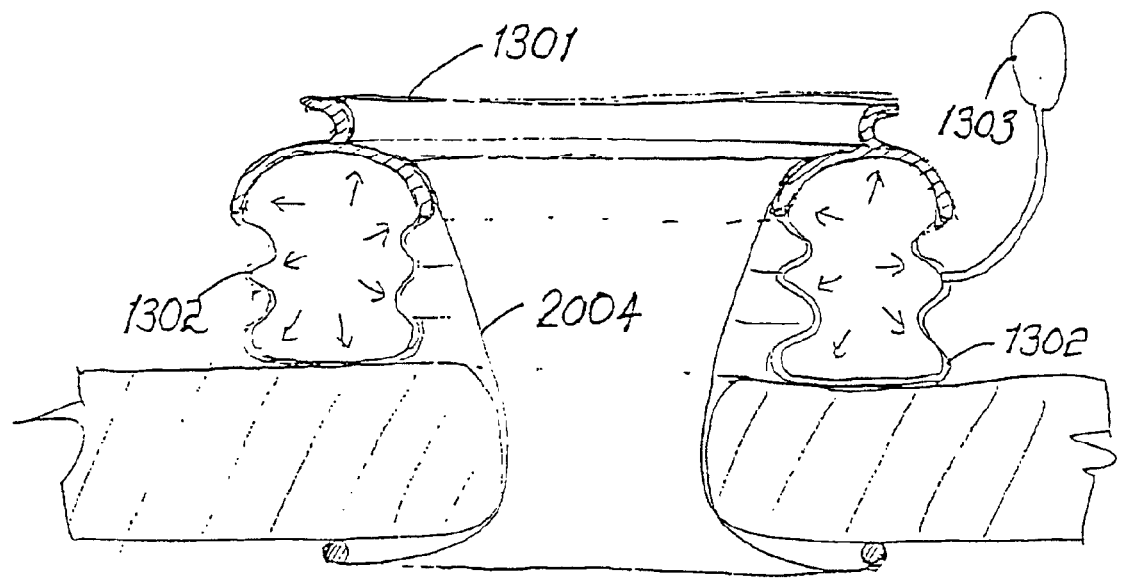
FIG. 19 is a sectional view of a further surgical device in accordance with the invention in position on a patient.
Figure 20:
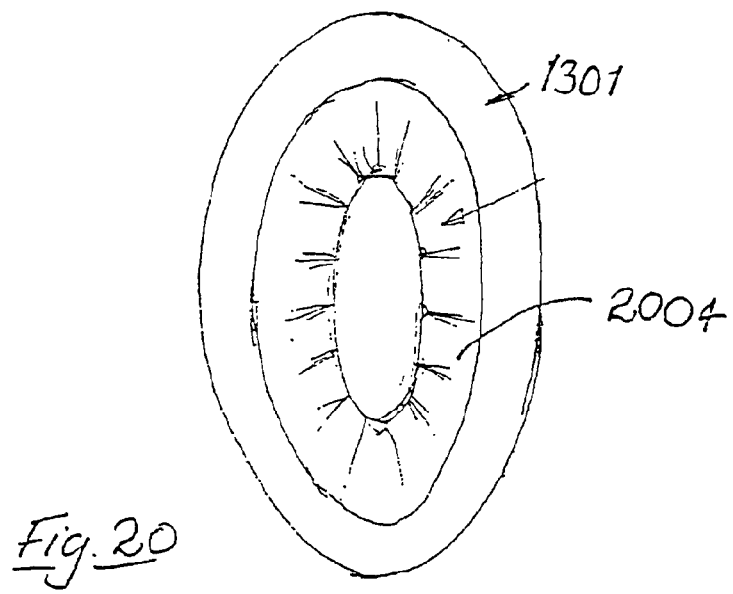
FIG. 20 is a top view of the surgical device of FIG. 19.

Referring now to FIGS. 19 and 20 there is illustrated another surgical device according to the invention, indicated generally by the reference numeral 1300 in which parts similar to those described in FIGS. 10 to 18 are identified by the same reference numerals generally. In this embodiment, the sleeve 2004 extends downwardly from an oval semi-rigid proximal ring 1301. The ring 1301 in turn is carried on an inflatable ring 1302, which is formed for inflation by an inflator 1303. In use, the device is positioned on a patient and the ring 1302 is inflated. The degree of retraction required is controlled by the pressure in the ring 1302 as greater pressure will force the sleeve 2004 against the incision. As the proximal, distal and inflatable rings are oval even pressure is applied at all points during retraction greatly reducing patient trauma. The inflation of the ring 1302 draws the sleeve 2004 against the incision and prevents loss of pneumoperitoneum.

Figure 21:
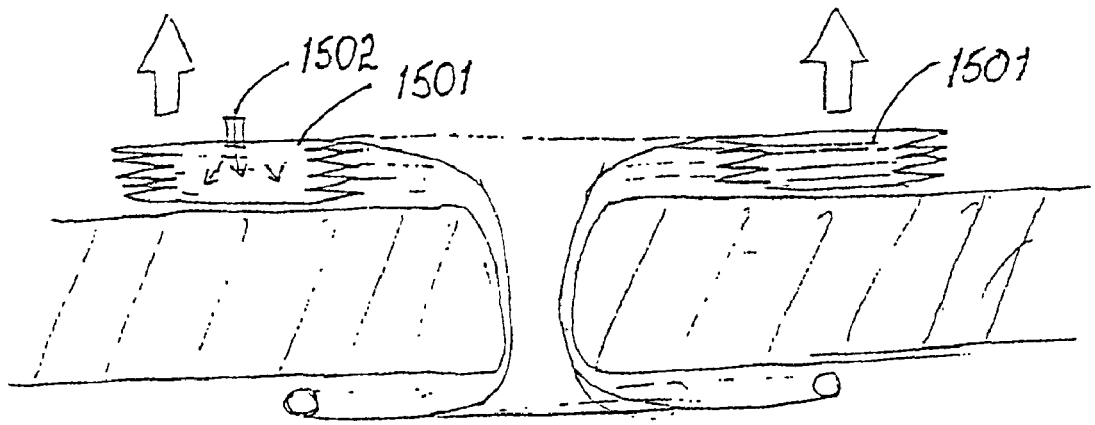
FIG. 21 is a sectional view of another surgical device in accordance with the invention in an insertion position on a patient.
Figure 22:
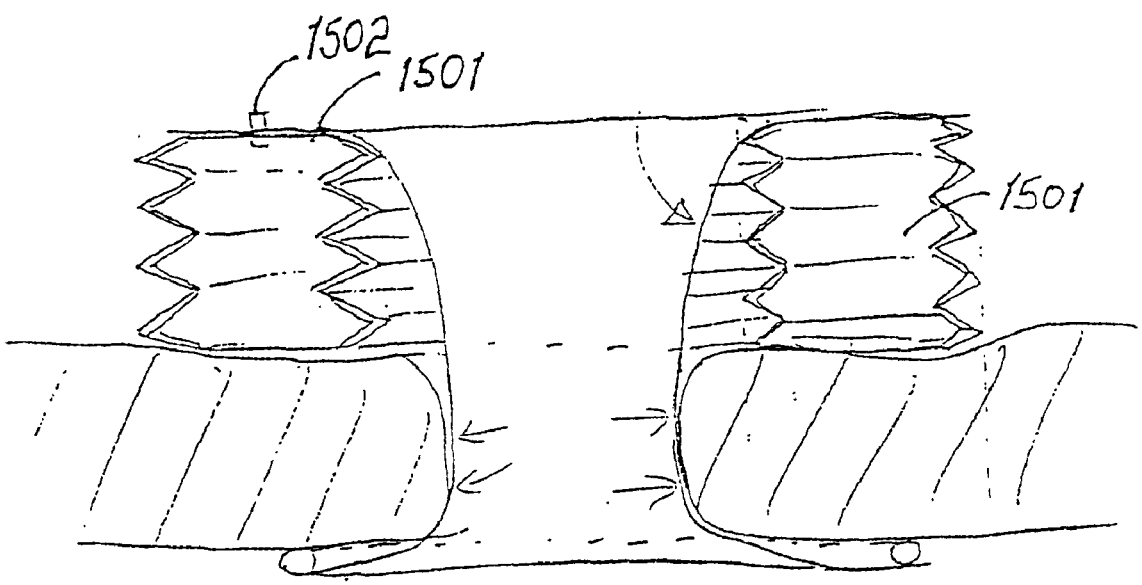
FIG. 22 is a sectional view of the surgical device of FIG. 21 in an operating position on a patient.

FIGS. 21 and 22 illustrate another surgical device according to the invention indicated as 1500, which is similar in operation to the embodiment shown in FIGS. 19 and 20. In this embodiment ring 1302 is replaced with a compressible bellows ring 1501. The bellows ring 1501 has a one-way valve 1502. In use, the compressed bellows ring 1501 is positioned on a patient. The ring is drawn up to allow air to inflate the bellows ring 1501 through the valve 1502. This inflation retracts the incision to the required degree and the valve 1502 prevents the air from escaping and the incision from closing. The incision can be released only by activation of the valve 1502 by the surgeon.

Thus, by the relatively simple expedient of providing an integrated wound or incision retractor in the access port, trauma is reduced thereby greatly easing patient suffering and accelerating postoperative recovery. Additionally, the invention provides a greater range of movement to the surgeon allowing the device to be used in a wider variety of surgical applications.

It will of course be understood that the invention is not limited to the specific details described herein, which are given by way of example only, and that various modifications and alterations are possible within the scope of the apended claims.

What is claimed is:

1. An access port device for use in surgery, comprising:
   a first sleeve of flexible material including a proximal end and a distal end;
   a securing device attached to said distal end of said first sleeve to secure the access port device externally to a patient;
   a second sleeve of flexible material attached to the proximal end of said first sleeve, said second sleeve including an entry opening adjacent said proximal end of said first sleeve and an exit opening positioned a spaced distance from said entry opening;
   an inflatable chamber formed between said first and said second sleeves;
   a third sleeve of flexible material attached to at least one of said first sleeve and said second sleeve, said third sleeve including an annular elastic band positioned between said entry and said exit openings of said second sleeve to sealingly engage a surgeon's arm extending through said third sleeve.

2. An access port device as claimed in claim 1, wherein said third sleeve is of a sufficient length to be positioned adjacent said exit opening.

3. An access port device as claimed in claim 2, wherein said third sleeve extends along a substantial portion of said second sleeve.

4. An access port device as claimed in claim 3, wherein said third sleeve is attached to said second sleeve at a first attachment location adjacent said entry opening and as a second attachment location a spaced distance along said second sleeve from said first attachment location.

5. An access port device as claimed in any preceding claim wherein said elastic band is positioned at a distal end of said third sleeve.

6. An access port device for use in surgery, comprising:
   a first sleeve of flexible material including a proximal end and a distal end;
   a securing device attached to said distal end of said first sleeve to secure the access port externally to a patient;
   a second sleeve of flexible material attached to the proximal end of said first sleeve, said second sleeve including an entry opening adjacent said proximal end of said first sleeve and an exit opening positioned a spaced distance from said entry opening for insertion into an incision formed in a patient's body;
   an inflatable chamber formed between said first and said second sleeves;
   an elongated exit opening seal mounted on said second sleeve at said exit opening, said exit opening seal positioned along an exit opening seal plane extending through said entry opening and said exit opening of said second sleeve;
   a second sleeve retraction prevention means for preventing inadvertent retraction of said second sleeve from the incision, said second sleeve retraction prevention means including at least one transverse wing extending transverse to said exit opening seal plane.

7. An access port device as claimed in claim 6, wherein said at least one transverse wing includes at least one first wing positioned on a first side of said exit opening and at least one second wing positioned on a second side of said exit opening.

8. An access port device as claimed in claim 7, wherein each of said at least one first wing and said at least one second wing includes a pair of wings.

9. An access port device as claimed in any of claims 6 to 8, wherein said at least one transverse wing is integrally formed on said elongated exit opening seal.

10. An access port device as claimed in any of claims 6 to 8, wherein said elongated exit opening seal includes a pair of opposed bands biased together, said at least one transverse wing integrally formed on at least one band of said pair of opposed bands.

11. An access port device as claimed in claim 10, wherein said at least one transverse wing includes a first pair of wings and a second pair of wings.

12. An access port device as claimed in claim 11, wherein said first pair of wings is located at a first end of said pair of opposed bands and said second pair of wings is located at a second end of said pair of opposed bands.

13. An access port device as claimed in claim 12, wherein one wing of said first pair and one wing of said second pair of wings extend from one band of said pair of opposed bands in a first transverse direction and the other wing of said first pair and the other wing of said second pair of wings extend from the other band in a second transverse direction opposite said first transverse direction.

* * * * *